United States Patent [19]

Hsueh et al.

[11] Patent Number: 5,365,559
[45] Date of Patent: Nov. 15, 1994

[54] PARTICLE COUNTING APPARATUS FOR A TOTAL COUNTING OF PARTICLES CONTAINED IN A LIQUID SAMPLE

[75] Inventors: Yu-Ming Hsueh; Kazumichi Imai; Masataka Koga, all of Katsuta, Japan

[73] Assignee: Hitachi, Ltd., Tokyo, Japan

[21] Appl. No.: 8,984

[22] Filed: Jan. 26, 1993

[30] Foreign Application Priority Data

Jan. 30, 1992 [JP] Japan ................................. 4-014825

[51] Int. Cl.$^5$ ...................... G01N 15/00; G01N 21/53; G06M 11/00
[52] U.S. Cl. ...................................... 377/10; 364/555; 356/40; 324/71.4
[58] Field of Search ............................. 377/10, 11, 12; 364/555; 356/40; 324/71.4

[56] References Cited

U.S. PATENT DOCUMENTS

| | | | |
|---|---|---|---|
| 4,330,745 | 5/1982 | Hayashi | 377/10 |
| 4,586,190 | 4/1986 | Tsuji | 377/10 |
| 4,835,703 | 5/1989 | Arnold et al. | 377/10 |
| 5,274,431 | 12/1993 | Kuroda | 377/10 |

Primary Examiner—John S. Heyman
Attorney, Agent, or Firm—Antonelli, Terry, Stout & Kraus

[57] ABSTRACT

A particle counting apparatus for counting a total particle counting value contained in a liquid sample comprising, a flow cell in which the liquid sample flows, a light source for irradiating a light beam to the sample liquid in the flow cell, a detector for detecting pulse-wise signal scattered from the particles by the irradiating of the light beam, and a computer for obtaining the total particle counting value contained in the liquid sample as a counting value measured when the top end of the liquid sample is irradiated with the light beam and the plural particles in the top end does not overlapped in the light beam, multiplied by a coefficient.

9 Claims, 5 Drawing Sheets

PARTICLE COUNTING APPARATUS FOR A TOTAL COUNTING OF PARTICLES CONTAINED IN A LIQUID SAMPLE

BACKGROUND OF THE INVENTION

The present invention relates to a particle counting apparatus for obtaining a total counting value of particles contained in a liquid sample or a density of the particles in the liquid sample, that is, a concentration of the sample by detecting a number of the particles contained in the sample which flows in a flow cell.

The light active particle counting apparatus for counting particles in the sample by irradiating a light beam or a laser beam to the particles and detecting a pulse-wise scattering light, fluorescence or sound wave from the particles in the sample which flows in a tube is widely known.

For example, Japanese Patent Laid-open Nos. 50-11290(1975) and 63-142234(1988) disclose particle counting apparatuses for counting the particles by irradiating the laser beam to the particles and detecting the scattering light from the particles.

Further, Japanese Patent Laid-open Nos. 50-68174(1975) (corresponding to U.S. Pat. No. 4,009,443) and 50-120880(1975) (corresponding to U.S. Pat. No. 3,864,551), and Review of The Scientific Instruments, Vol. 43(1972), pp 1407–1412, disclose correcting methods of a particle counting error which arises when plural particles are simultaneously passed through a detection light beam. However, as such correcting methods are performed based on an estimation of the error by detecting a uniform flow of the sample, it is difficult to expect an accurate particle counting.

Japanese Patent Laid-open No. 2-162234(1990) discloses a particle counting method which counts not only a uniform density portion of the sample flow, but also a top end and last end of the sample flow by dividing the sample flow with time and detecting particles in the divided flows. However, such reference does not show how to correct for saturation of the counting value when plural particles irradiated with a light beam so as to be counted are overlapped in the light beam. Accordingly, there is a problem relating to an accurate estimation of the particle counting in the end portions of the sample flow.

SUMMARY OF THE INVENTION

An object of the present invention is in providing a particle counting apparatus for accurately detecting the total counting value of particles such as blood corpuscle, dust, etc., contained in a liquid sample such as blood, water etc.

In order to solve the above problem, the present invention sets a checking term at an initial (i.e., top) portion of the flow of liquid sample in a flow cell. In this portion, plural particles in the liquid sample are not overlapped until a certain high concentration is achieved when passing through a detection light beam. A coefficient of correlation is obtained between the counting values at the check point and the point within a uniform portion, or between the values counted from the time of start to the check point and to the end point at which all of particles past through detector. An accurate total counting value of the particles in the sample can be determined by normalization of the counting result at a check point using the coefficient obtained as above.

In the present invention, the above checking term is used so as to mean one point of the time (said frequency method) and/or a period of the time.

DETAILED DESCRIPTION OF THE PREFERRED EMBODIMENT

Figure 2:
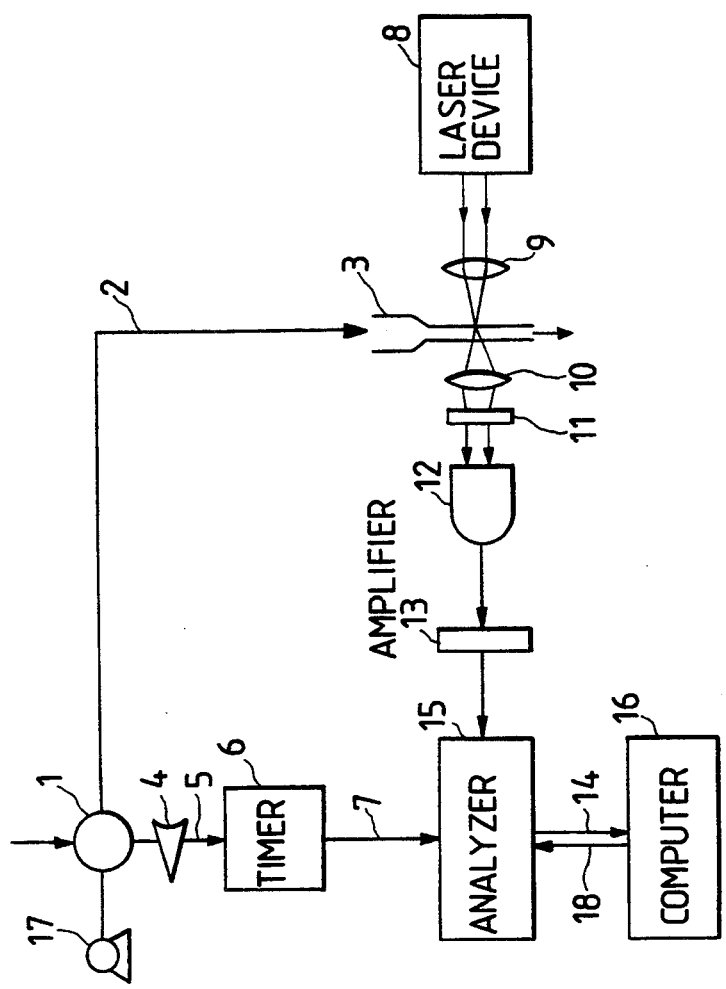
FIG. 2 is an schematic view of an embodiment of a particle counting apparatus according to the present invention.

An embodiment of total construction of a particle counting apparatus in the present invention is described below by referring to FIG. 2.

A liquid sample is injected from a sample injector 1, is transmitted through a tube 2 by a pump 17 and is supplied to a flow cell 3, as the liquid sample is injected into rinsing liquid supplied from the pump 17 by the injector 1 and the liquid sample in the tube 2 is contacted with the rinsing liquid at a leading (i.e., top) end and a concluding (i.e., last) end of the sample liquid.

The rinsing liquid is used for rinsing the flow cell 3 and is used as a blanking liquid for obtaining a counting value for calibration in blank measuring.

A laser beam emitted from a laser device 8 is converged by a lens 9 so that the liquid sample in the flow cell 3 is partially passed through the converged laser beam.

A pulse-wise scattered light or fluorescence generated from the particles in the liquid sample when the liquid sample is passed through the laser beam is gathered by a lens 10 and is passed through a filter 11 so as to be detected with a photo-multiplier 12.

Instead of the laser beam, a different optical beam or sound beam may be irradiated to the particles and optical signals or acoustic signals scattered from the particles may be detected by a suitable detector instead of the photo-multiplier 12.

An output signal from the photo-multiplier 12 which is proportional to a particle number f contained in the liquid sample is amplified by an amplifier 13 and supplied to a pulse analyzer 15 which counts the particle number and outputs a signal 14 corresponding to the particle number by analyzing the output signal from the photo-multiplier 12.

Figure 3:
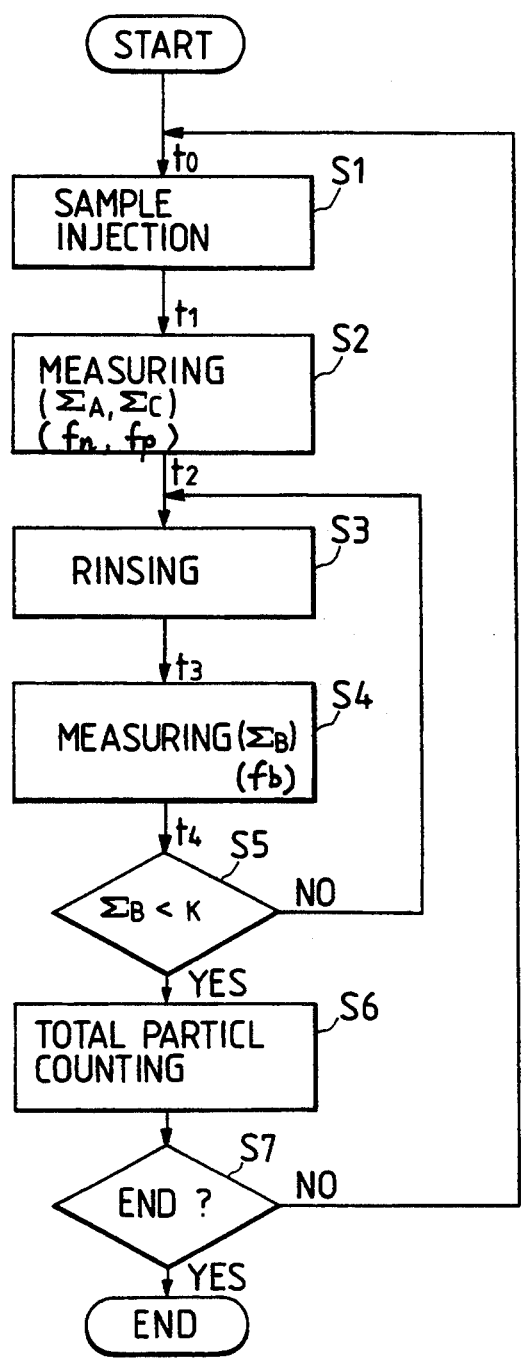
FIG. 3 is an example of a flow chart which shows the counting method in the present invention.

A computer 16 processes the signal 14 from the analyzer 15 as shown in a flow chart of FIG. 3 and displays the processed data of the signal 14, that is, the total counting values or "error" signal.

A switch 4 is operated by detecting a timing of injection of the sample by the sample injector, and generates a trigger signal 5. A timer means 6 generates timing signals at a starting time $t_1$ for starting to analyze the output signal measured by the photo-multiplier 12, a checking time $t_n$ and a finishing time $t_2$ for finishing to analyze the output signal.

Figure 1A:
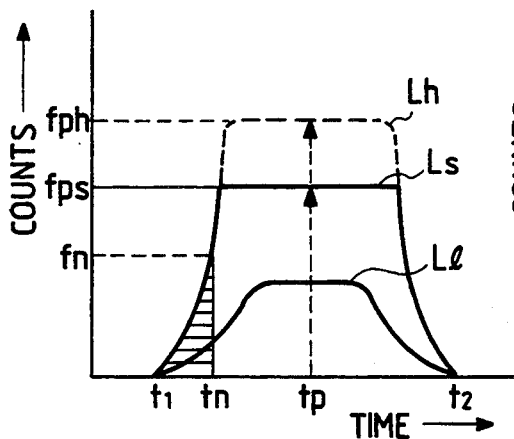
FIGS. 1A, 1B, 1C, 1D are schematic views which show a conception of a counting method of the particles contained in a liquid sample in the present invention.
Figure 1C:
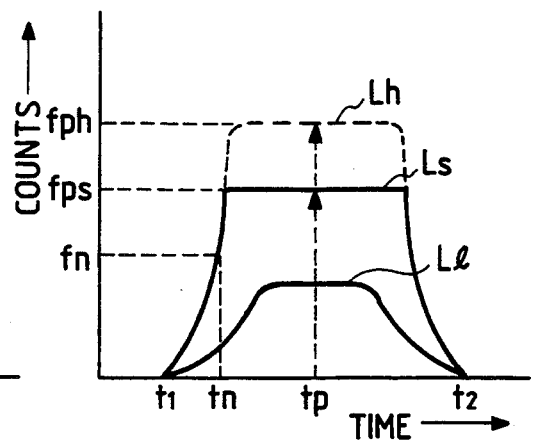

In the particle counting apparatus as stated above, a conception of the counting method of the particle in the present invention is explained using FIGS. 1A, 1B, 1C, 1D as follows;

FIGS. 1A and 1C show the variation of particle counts f detected by the photo-multiplier 12 with respect to time. A curve $L_l$ shows a profile of the sample with low particle density. The particles in this sample are not overlapped When passing through the detection beam generated from the laser device 8.

The sample will be diluted at the leading end and the concluding end of the liquid sampling because of the diffusion of the particle to the carrier liquid. Therefore, the particle number f is gradually increased from zero at the leading end of the liquid sample, then a uniform particle number is detected during a steady-state region to form a flat portion on which the particle density is uniform, and the particle number is gradually decreased at the concluding end of the liquid sample so as to become zero at the last.

In the flat portion of the curve $L_l$, as the particles are not overlapped when passing through the laser beam, the particle number f, that is, the counting value of the particles is proportional to a real particle number contained in the sample.

When the particle density in the sample increases plural particles pass through the detection beam simultaneously, and would be counted as one particle by the detector so that a profile $L_s$ is obtained instead of $L_h$.

A timer 6 is used for controlling the timing of the measurements of the particles in sample.

The timer 6 sends a signal for starting a count of the particles in the liquid sample when a predetermined time has elapsed after receiving the trigger signal from the switch 4 and the leading end of the liquid sample has just reached the detector at the same time $t_1$.

The timing signal for checking time $t_n$ is set by the timer 6 so as to be generated after the timing signal for the starting time $t_1$ is generated and before the photo-multiplier 12 begins to detect the overlapped particles in the sample having a high density of particles.

The timing signal for finishing time $t_2$ is set by the timer 6 when the concluding end of the liquid sample passes through the flow cell 3 and to stop the counting of the particles.

The object of the present invention is in obtaining the total counting value of the particles which is usually obtained by integrating the counting value f on the curve L from time $t_1$ to time $t_2$.

Figure 1B:
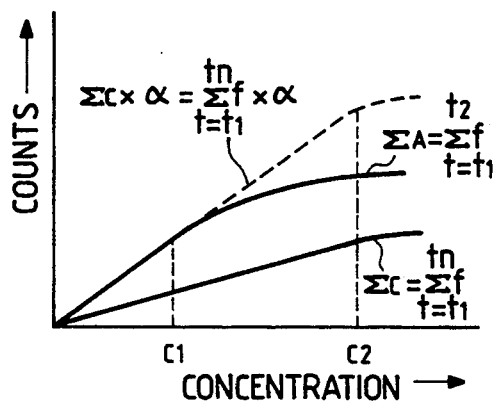
Figure 1D:
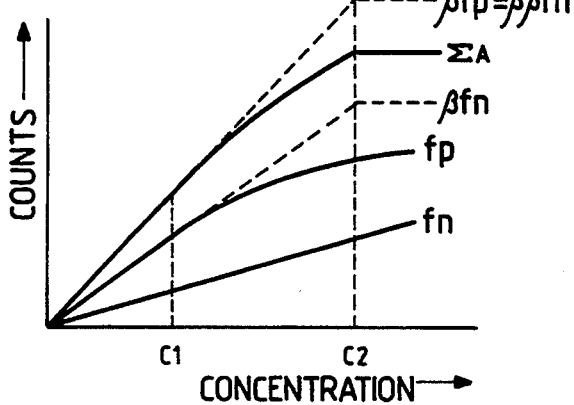

But, the total particle counting value $\Sigma A$ obtained by integrating the curves from time $t_1$ to time $t_2$ is saturated when the particle density larger than a certain value, that is, the concentration of the liquid sample is higher than a certain concentration $C_1$ as shown in FIG. 1B. Therefore, an accurate particle number contained in the liquid sample is not obtained. As embodiments in the present invention, two methods, i.e., an integration method and frequency method, are provided. In the integrated method, when the concentration of the liquid sample is over the concentration $C_1$, an integrated counting value $\Sigma C$ is monitored simultaneously with $\Sigma A$ from the starting time $t_1$ to the checking time $t_n$. The counting value of any liquid sample is still unsaturated at the time $t_n$. There is a certain correlation between the counting values $\Sigma C$ and $\Sigma A$ for unsaturated samples, and a coefficient $\alpha$ ($\alpha = \Sigma A/\Sigma C$) of the correlation may be obtained using the results of a and $\Sigma C$, the total counting value $\Sigma A$ as $\alpha \Sigma C$ for such samples with a concentration higher than $C_1$.

Therefore, the real total particle counting value is linearly increased in proportional to the concentration of the liquid sample as shown with a dotted line in FIG. 1B. An accurate total particle counting value of the liquid sample is obtained as a value $\alpha \Sigma C$ by previously measuring the correlation coefficient $\alpha$ and the counting value $\Sigma C$ integrated from the starting time $t_1$ to the checking time $t_n$ of the leading part of the liquid sample at which the counting value linearly increases with the concentration of samples.

Similarly in FIG. 1C, when the particle density is over $C_1$, instead of $f_{ph}$ a counting value $f_{ps}$ will be measured at the time $t_p$ on the flat portion of the curve $L_h$.

In the frequency method, when the concentration of the liquid sample is over $C_1$, a counting value $f_n$ is monitored simultaneously with $f_p$ and $\Sigma A$ at the checking time $t_n$.

There is a certain correlation between the counting values $f_n$ and $f_p$ for samples with particle density lower than $C_1$, and a coefficient $\beta$ ($\beta = f_p/f_n$) of the correlation between the counting value $f_n$ in the leading end and the counting value $f_p$ in the flat portion can be obtained. Therefore, the real particle number passing through flow cell at time $t_p$ is obtained as a product of the counting value $f_n$ and the correlation coefficient $\beta$, linearly increased in proportional to the concentration of the liquid sample as shown with a dotted line in FIG. 1D.

In addition, a relation is held between the counting values $f_p$ and $\Sigma A$ as $\Sigma A = \beta' f_p$ when the sample concentration is lower than $C_1$. The coefficient $\beta'$ is obtained by monitoring simultaneously the values of $f_p$ and $\Sigma A$ with low concentration ($<C_1$) samples. Therefore the real total counting value may be calculated as the product of $f_p$ and $\beta'$ as well as $\beta' \beta f_n$.

By the way, the counting value at the starting time $t_1$ is 0 or 1 usually, but the counting value in the case the time $t_1$ closest to the time $t_n$ and is before the time $t_n$ is not 0 or 1, but is available to the present invention. When the time $t_1$ which is delayed is equal to the time $t_n$, the coefficient $\alpha$ becomes equal to the coefficient $\beta \beta'$.

Based on the above stated conception of the particle counting methods, the total counting value of the liquid sample is practically obtained according to flow charts performed computer 16 shown in FIGS. 3 and 4.

In FIG. 3, at a step S1, the timer 6 starts to operate at time $t_0$ by receiving a trigger signal from the switch 4 which detects a timing of the sample injection of the injector 1.

At a time $t_1$, after a predetermined time has elapsed from the time $t_0$, the top portion of the liquid sample injected from the injector 1 gets to the laser beam in the flow cell 3 and the particles begins to be counted at step S2. At the step S2, the counting values $\Sigma A$, $\Sigma C$, $f_p$ and $f_n$ are measured as stated above by receiving the timing signals of the starting time $t_1$, the checking time $t_n$ and the finishing time $t_2$ from the timer 6.

After measuring the counting values $\Sigma A$, $\Sigma C$, $f_p$ and $f_n$ the flow cell 3 is rinsed by the carrier liquid transmitted through the tube 2 at step S3.

Then, the blank measurements are carried out at the step S4 to obtain the blank counting values $\Sigma B$ from $t_3$ to $t_4$ ($t_4 - t_3 = t_2 - t_1$) and $f_b$ and $t_n$.

At step S5, when the blank counting value $\Sigma B$ is below a certain value K, which is predetermined experimentally, the rinsing of the flow cell is judged to be perfect and next step S6 is performed. When the value $\Sigma B$ in the blanking measuring is not below the certain value K, the rinsing of the flow cell is judged not to be perfect and the step S3 is again performed.

At step S6, the total particle counting value is calculated, and after finishing the calculation, whether another particle counting relating to the another sample should be performed or not is judged at a step S7.

Figure 4A:
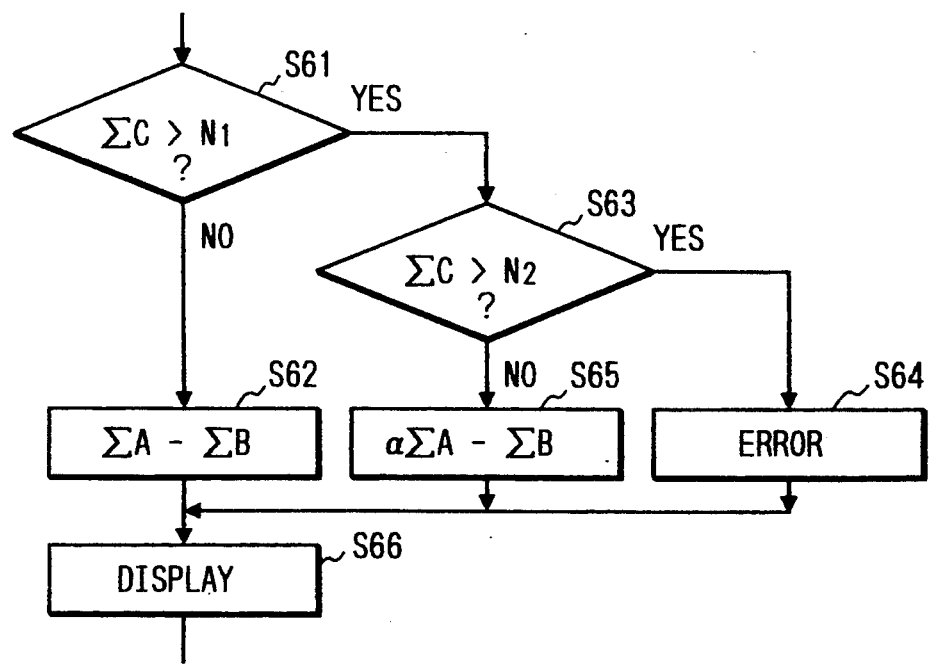
FIGS. 4A and 4B are detailed flow charts of the calculating step S6 shown in FIG. 3.
Figure 4B:
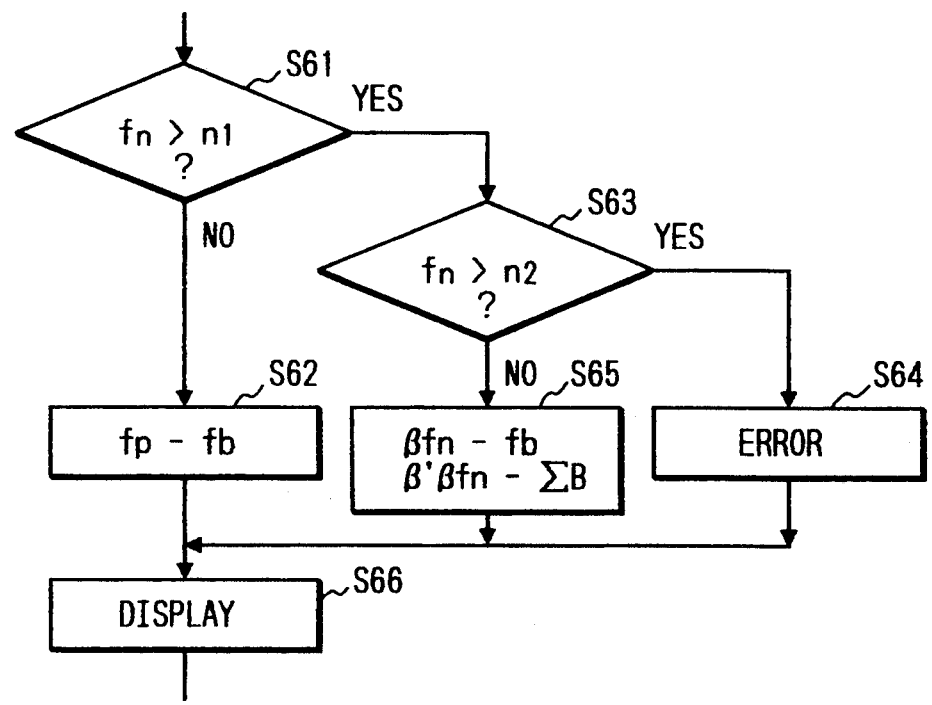

Detailed flow charts of the step S6 in the FIG. 3 are shown in FIGS. 4A and 4B.

In FIGS. 4A and 4B, the sample concentration is first judged at step S61. Then the particle counting value $\Sigma C$ for integration method (FIG. 4A) or $f_n$ for frequency method (FIG. 4B) of the sample liquid at the check time is judged not to be over the value $N_1$ ($n_1$ respectively) which is predetermined by counting the sample with concentration $C_1$ at which the particles in the liquid sample begins to overlap in the laser beam. Finally, the counting value is simply obtained as a difference between the total particle counting value $\Sigma A$ and the blank counting value $\Sigma B$ at step 62.

When the particle counting value $\Sigma C$ or $f_n$ is larger than $N_1$ or $n_1$ respectively, the sample is judged to have a concentration over $C_1$ and the data normalization becomes necessary for obtaining accurate counting values. Then the value $\Sigma A$ (FIG. 4A) or $f_n$ (FIG. 4B) is further compared with the values $N_2$ and $n_2$ respectively at step S63.

$N_2$ and $n_2$ are the counting values experimentally predetermined with the sample of concentration $C_2$. The concentration $C_2$ means a concentration which is larger than the concentration $C_1$ and is so large that an accurate total particle counting value of the liquid sample is not obtained even though the normalization is performed.

Then $\Sigma C < N_2$ (FIG. 4A) and/or $f_n < n_2$ (FIG. 4B), the total particle counting value is obtained as a difference between the product of $\alpha$ and $\Sigma C$ and the blank counting value $\Sigma B$ (FIG. 4A), and/or as a difference between $\beta'\beta f_n$ and $\Sigma B$ (FIG. 4B) for total counting and between $\beta f_n - f_b$ for frequency counting at step S65.

When the sample is judged over the concentration $C_2$, an error message is indicated at step S64 and the dilution of the sample is performed by a control of the computer.

The counting results at steps S62, S64 and S65 are displayed at step 66 (FIGS. 4A and 4B).

Figure 5:
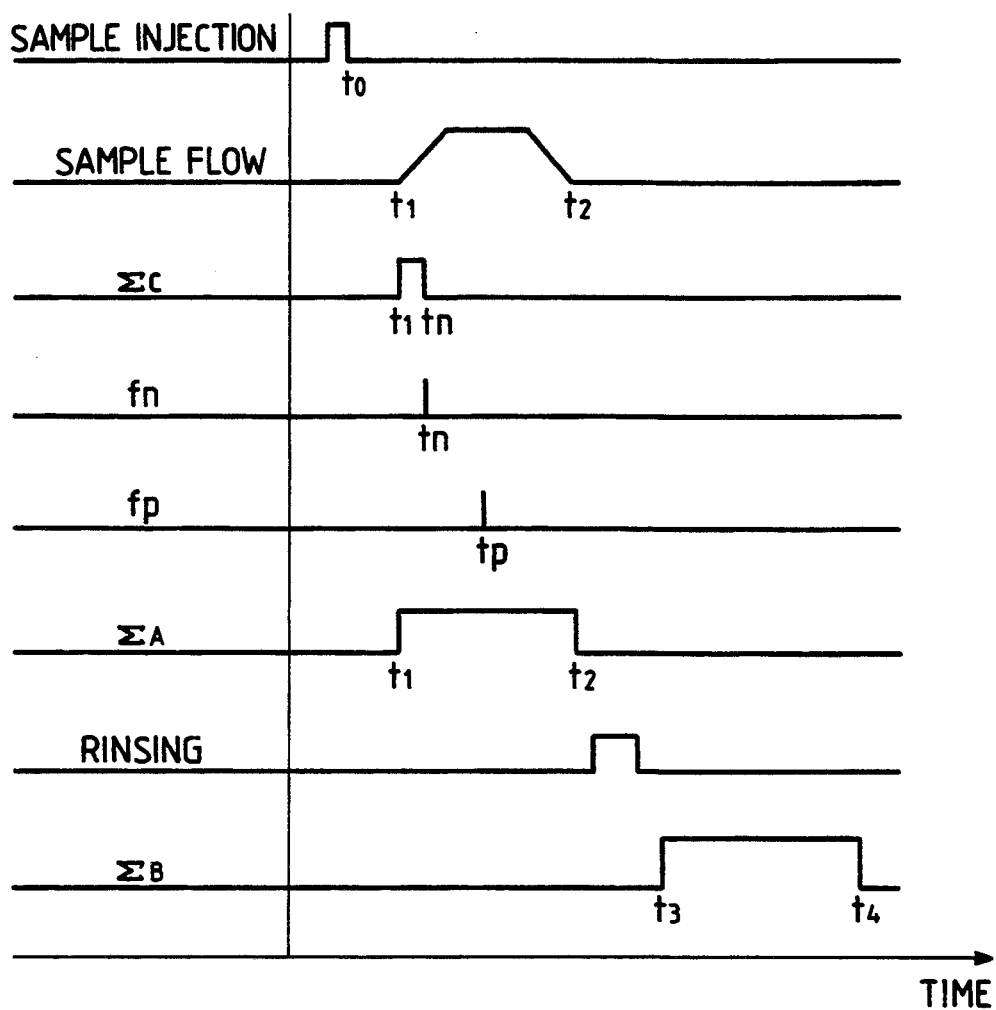
FIG. 5 is a timing chart of the counting method of the present invention.

FIG. 5 shows an example of a timing chart of the operation performed based on the flow charts shown in FIGS. 3 and 4.

As shown in FIG. 5, after the liquid sample is injected at the time $t_0$, the liquid sample begins to flow and the timer starts. At the time $t_1$, the sample reaches to detector and the particle counting values $\Sigma C$, $\Sigma A$ begins to be counted. The measurements of $f_n$ and $f_p$ are achieved at times $t_n$ and $t_p$ respectively within the time $t_2$, at which all of the sample is past through the detector and the particle counting is discreated. After that, the rinsing process of the flow cell 3 and the blank measurement $\Sigma B$ are taken place one after another.

We claim:

1. A particle counting apparatus for counting particles contained in a liquid sample comprising,
    a flow cell in which the liquid sample flows,
    a light source for irradiating a light beam to the sample liquid in the flow cell,
    a detector for detecting a pulse-wise signal scattered from the particles by the irradiating of the light beam thereto, and
    a computer for obtaining a total particle counting value by multiplying a first counting value obtained by counting the particles in the liquid sample when a leading portion of the liquid sample flowing through said flow cell is irradiated with the light beam and the plural particles in the leading portion do not overlap in the light beam, with a correlation coefficient which is previously obtained as a correction value based on a relation between said first counting value and a second counting value obtained by counting the particles when a steady-state portion of the liquid sample is irradiated with the light beam.

2. A particle counting apparatus as defined in claim 1, wherein said computer is arranged to obtain the total particle counting value by integrating the first counting value from a starting time for starting to count particles when the leading portion begins to be irradiated to a predetermined checking time after the starting time.

3. A particle counting apparatus as defined in claim 1, wherein said computer is arranged to obtain the total particle counting value by determining the first counting value at a checking time when the leading portion is finally irradiated.

4. A particle counting apparatus as defined in claim 1, further comprising,
    a timer for generating timing signals generated at a starting time for starting to measure the particle counting at the leading portion of the liquid sample, a checking time after the starting time at which the plural particles do not overlap in the light beam and a finishing time for finishing measurement of the particle counting at the leading portion.

5. A particle counting apparatus as defined in claim 1, wherein said computer is arranged to measure a blanking measurement value for correcting the total particle counting value of the sample by subtracting a particle counting value in the blanking measurement value from the total particle counting value.

6. A particle counting apparatus as defined in claim 1, wherein said computer is arranged to determine the total particle counting value of the liquid sample as the first counting value multiplied by the correlation coefficient in a case where the sample exceeds a concentration of the liquid sample at which plural particles begin to overlap in the light beams and as an integrated counting value integrated from a leading portion of the liquid sample up until a concluding portion of the liquid sample in a case where the sample does not exceed the concentration the liquid sample at which plural particles begin to overlap in the light beam.

7. A particle counting apparatus as defined in claim 6, further comprising,
    a display for showing an error information when the counting value measured at the leading portion of the liquid sample exceeds the concentration of the liquid sample at which plural particles begin to overlap in the light beam.

8. A particle counting apparatus as defined in claim 7, wherein said computer is arranged to control delivery of the liquid sample so as to dilute the liquid sample.

9. A particle counting apparatus as defined in claim 7 wherein said detector detects the pulse-wise signal of an optical signal or signal.

* * * * *